United States Patent [19]

Gerhards et al.

[11] Patent Number: 5,703,284
[45] Date of Patent: Dec. 30, 1997

[54] DEVICE FOR TESTING NON-UNIFORM WEAR ON TREAD STRIPS OF PNEUMATIC VEHICLE TIRES

[75] Inventors: Bernhard Gerhards, Aachen; Hans-Jürgen Krutt, Monschau; Wilhelm Thissen, Stolberg, all of Germany

[73] Assignee: Uniroyal Englebert Reifen GmbH, Aachen, Germany

[21] Appl. No.: 609,393

[22] Filed: Mar. 1, 1996

[30] Foreign Application Priority Data

Mar. 3, 1995 [DE] Germany ............ 195 07 441.6

[51] Int. Cl.$^6$ ............ E01C 23/00; G01M 17/02
[52] U.S. Cl. ............ 73/146
[58] Field of Search ............ 73/7, 8, 9, 146; 51/106 R, 281 R; 157/14, 16, 20, 21; 364/463, 506, 508

[56] References Cited

U.S. PATENT DOCUMENTS

| 535,799 | 3/1895 | Heim. | |
|---|---|---|---|
| 3,604,245 | 9/1971 | Atelian. | |
| 3,726,124 | 4/1973 | Obarski | 73/8 |
| 3,977,243 | 8/1976 | Yamada et al. | 73/146 |
| 4,344,325 | 8/1982 | Iwama | 73/146 |
| 4,489,598 | 12/1984 | Beebe et al. | 73/146 |
| 4,848,143 | 7/1989 | Ushikoshi | 73/146 |

FOREIGN PATENT DOCUMENTS

| 2306563 | 2/1973 | Germany. |
|---|---|---|
| 2611123 | 3/1976 | Germany. |
| 2831978 | 7/1978 | Germany. |

Primary Examiner—George M. Dombroske
Assistant Examiner—William L. Oen
Attorney, Agent, or Firm—Robert W. Becker & Associates

[57] ABSTRACT

A device for simulating non-uniform wear on a tread strip of a pneumatic vehicle tire has a support structure and a friction body with radially symmetry connected to the support structure so as to be rotatable about a first axis of rotation. The friction body has a rigid circumferential mantle surface with a continuous, permanent friction coating. A receptacle is rotatably connected to the support structure for receiving a vehicle wheel with pneumatic vehicle tire. The vehicle wheel is rotated about a second axis of rotation with the receptacle. A load applying member is connected to the receptacle and extends radially relative to the friction body. It acts radially onto the receptacle for pressing the pneumatic vehicle tire onto the friction coating for generating wear at the pneumatic vehicle tire. A first control device for pivoting the second axis of rotation of the vehicle wheel about a first pivot axis is provided. The first pivot axis extends perpendicular to the first axis of rotation. Pivoting occurs from a position parallel to the first axis of rotation into a position at an angle to the first axis of rotation for simulating a positioning angle of the vehicle wheel such as camber angle and kingpin inclination angle.

14 Claims, 2 Drawing Sheets

DEVICE FOR TESTING NON-UNIFORM WEAR ON TREAD STRIPS OF PNEUMATIC VEHICLE TIRES

FIELD OF THE INVENTION

The present invention relates to a device for testing non-uniform wear of tire tread strips of a pneumatic vehicle tire.

BACKGROUND ART

For determining and testing the quality as well as the performance of pneumatic vehicle tires it is conventional to perform extensive tests and observations of the pneumatic vehicle tire mounted on vehicles during driving. Such tests, however, are very time-consuming and, due to the various influences that are difficult to separate from one another and overlap one another, are difficult to evaluate with respect to individual parameters of interest. For concrete examinations of properties and behavior of tires under certain preset conditions for a better understanding of the various influences on the pneumatic vehicle tire and of the behavior of the pneumatic vehicle tire as well as with respect to improvements with respect to tire quality to be derived therefrom, tires are also tested on special test stands, for example, for determining the rolling resistance or for testing the continuous stress behavior during continuous operation. The test stands for determining the rolling resistance as well as the test stands for testing the long term loadability are designed such that the determination of possible disruptive wear behavior of the pneumatic vehicle tire is minimized. Conventionally, such stands are provided with rigid, rotatable receptacles for the vehicle wheel that is pressed for testing against a substantially smooth, conventionally ground, steel surface of a rotating roller. For the purpose of rolling resistance measurements the measuring devices are arranged within rigid wheel receiving units. Either the vehicle wheel or the rotating roller is driven. With an exactly defined pressure force acting radially to the roller, rolling resistance measurements are performed over short periods of time. From the determination of the rotational velocity of the tire and the driving forces, the drive loss and the rolling resistance are determined. In order to arrive at unambiguous reliable information with respect to the rolling resistance, the drive loss due to friction between the vehicle wheel and the roller must be essentially eliminated. Also, for continuous stress testing the loading with radial pressure forces, acting on the tire of the vehicle when driven on road surfaces, as well as their effect on the behavior of the construction of the vehicle tire are examined whereby any additional forces, for example, frictional forces acting on the tire will disturb and falsify the results.

Of increasing importance, in addition to the rolling resistance and the continuous stress testing of a tire, is the information of non-uniform wear of the tread strip of the vehicle tire under certain preset conditions for the purpose of designing optimized tread strips. Non-uniform wear, be it on individual block elements of the tread, be it over the entire width or in the circumferential direction of a tire, will result in different noise, traction, and wet grip behavior of the tire over the course of its service life. For simulating and testing non-uniform wear, test stands have been used in the past in which a rotating drive drum with thin emery paper at its circumferential surface is used.

Against the drive drum the pneumatic vehicle tire is radially inwardly pressed by radially outwardly positioned devices. The drive drum frictionally drives the rotatably supported vehicle wheel. The rough coating of emery paper results in wear and the worn off particles are bound with talc and removed by suction from the vehicle wheel. After extended testing intervals the wear pattern of the respectively tested tire tread strip can then be examined in regard to uniformness. Such test stands have the disadvantage that the roughness of the thin emery paper changes quickly in a non-predictable manner. The conditions for generating wear are thus changed already during the testing of one vehicle tire in a non-determinable, non-reproducible manner. The running conditions for a plurality of vehicle tires to be tested in sequence are thus not adjustable in an identical manner for each tire. The fast wear of the emery paper also requires frequent exchange of the emery paper so that the test results will become even more inexact. The non-defined exchange between a very rough emery paper surface and a non-defined worn surface of the emery paper is worsened by the sudden change to a very rough surface of new emery paper. Thus, due to the undefined quickly changing surface properties the quality of the measuring results is only satisfactory within limits. The test results of a plurality of tests of vehicle tires of the same construction performed in sequence and under assumed identical testing condition thus results in relatively high result fluctuations. The non-uniform testing conditions are worsened by the gap areas which result from the emery paper mounted across the circumferential surface of the friction drum which abut one another with their end sections. Such gap areas result in additional undesirable disturbances within the circumferential surface of the friction drum. Due to slight impacts on the tire, such gap areas can cause the vehicle tire to perform undesirable vibrations and the tire may demonstrate relative to the remaining circumference of the wear friction, a different wear behavior for these areas.

It is therefore an object of the present invention to provide a device for testing non-uniform wear at tread strips of pneumatic vehicle tires which affords for more precise testing results.

SUMMARY OF THE INVENTION

The inventive device for simulating non-uniform wear on a tread strip of a pneumatic vehicle tire according to the present invention is primarily characterized by:

A support structure;

A friction body having radial symmetry connected to the support structure so as to be rotatable about a first axis of rotation;

The friction body having a rigid circumferential mantle surface with a circumferentially continuous, permanent friction coating;

A receptacle rotatably connected to the support structure for receiving a vehicle wheel including a pneumatic vehicle tire, wherein the vehicle wheel is rotated about a second axis of rotation with the receptacle;

A load-applying member connected to the at least one receptacle;

The load-applying member extending radially relative to the friction body and acting radially onto the receptacle for pressing the pneumatic vehicle tire of the vehicle wheel onto the friction coating for generating wear at the pneumatic vehicle tire; and A first control means for pivoting the second axis of rotation of the vehicle wheel about a first pivot axis, extending perpendicular to the first axis of rotation, from a position parallel to the first axis of rotation into a position at an angle to the first axis of rotation for simulating a positioning angle of the vehicle wheel selected from a camber angle and a kingpin inclination angle.

Advantageously, the device further comprises a second control means for pivoting the second axis of rotation of the vehicle wheel about a second pivot axis, extending perpendicular to the first axis of rotation and in a common plane with the first pivot axis, from a position parallel to the first axis of rotation into a position at an angle to the first axis of rotation, wherein the first and second control means act independently on the receptacles such that pivoting about the first pivot axis simulates the camber angle and pivoting about the second pivot axis simulates the kingpin inclination angle.

Advantageously, a plurality of receptacles with coordinated load-applying members and first and second control means are distributed about the circumference of the friction body.

Preferably, six of the receptacles with six load-applying members and six first and six second control means are provided. Preferably, the friction coating is tamped or cast onto the friction body.

Preferably, the friction coating is comprised of abrasive emery cloth. In the alternative, the friction coating is comprised of grindstone material.

Advantageously, the friction coating may be comprised of broken corundum embedded in a potting resin.

In yet another embodiment of the present invention the friction body may comprise a steel mantle permanently coated with the friction coating.

The friction coating preferably has a radial thickness of 8 mm to 12 mm.

The first and second control means are preferably controllable pivot drives.

Preferably, the friction body is also controllable.

Inventively, the object of the present invention is solved by embodying the device for simulating and testing nonuniform wear at tread strips of vehicle tires by providing a friction body having radial symmetry and connected to the support structure so as to be rotatable about a first axis of rotation. The friction body has a rigid circumferential mantle surface with a circumferential continuous, permanent friction coating. A receptacle is rotatably connected to the support structure for receiving a vehicle wheel with a pneumatic vehicle tire. The vehicle wheel is rotated about a second axis of rotation with the receptacle. A load-applying member is connected to the receptacle and extends radially relative to the friction body and acts radially onto the receptacle for pressing the pneumatic vehicle tire of the vehicle wheel onto the friction coating for generating wear at the pneumatic vehicle tire. A first control means for pivoting the second axis of rotation of the vehicle wheel about a first pivot axis, extending perpendicular to the first axis of rotation, from a position parallel to the first axis of rotation into a position at an angle to the first axis of rotation is provided for simulating a positioning angle of the vehicle such as camber angle and kingpin inclination angle.

The vehicle wheel with its axis of rotation is pivotable about an axis that is perpendicular to its axis of rotation. Depending on the position of the pivot axis in the plane perpendicular to the axis of the vehicle wheel, conventional camber angles or kingpin inclination angles or a combination of camber and kingpin inclination angles can be adjusted by pivoting. Wear tests can thus be performed under realistic conditions. By embodying a rigid mantle surface of the friction body over its entire circumferential surface with a permanent, closed frictional coating the disadvantageous quick wear of the emery paper, as known from conventional devices and resulting in a non-defined state of a substantially smooth friction surface, is thus already considerably improved. The permanent friction coating provides for a substantially improved maintenance of a predetermined defined frictional state. Due to the closed (continuous) embodiment of the friction coating over the entire circumferential surface, gaps, resulting from transitions between abutting emery paper strips, respectively, gaps between the strips, caused by abutting arrangement of the free ends of the emery paper strips, are no longer present. Thus, with a device according to the present invention a vehicle tire can be subjected over the entire testing period to substantially constant, defined wear conditions. Sequential testing of vehicle tires can thus be performed substantially under the same defined testing conditions.

Thus, the testing results are substantially constant and reproducible. In addition, it is possible to make the testing conditions even more uniform when the permanent friction coating is embodied so as to be renewable. Even though the changes of such permanent friction coatings in comparison to changes resulting with thin emery paper coatings are very minimal, the slight changes that may appear, for example, by settling of worn-off particles after extended testing periods, can be changed by reworking the friction surfaces into a predetermined state. For an improved simulation over an especially wide range of camber angles and kingpin inclination angles, it is possible to adjust the pivot axis in its plane perpendicular to the axis of rotation of the vehicle wheel by rotation about the axis of rotation.

Advantageously, the receptacle for the vehicle wheel is embodied such that it is controllable for pivoting about a pivot axis for adjusting the camber angle as well as pivotable about a pivot axis for adjusting the kingpin inclination angle. This allows for a simple, but realistic positioning of the vehicle wheel with respect to driving conditions for all types of vehicle suspensions.

The arrangement of a plurality of inventive receptacles about the circumference of the friction body allows for simulating the non-uniform wear of a plurality of vehicle tires, even different types of vehicle tires, at the same time under same simulation conditions. By embodying the vehicle wheel receptacles with independently controllable pivot axes, it is also possible to adjust different camber angles and/or kingpin inclination angles at the simultaneously tested vehicle wheels. Preferably, the inventive device is provided with six vehicle wheel receptacles uniformly distributed over the circumference of the friction body. This also allows for an advantageous combination of three testing series with respectively two identical vehicle tires under the same testing conditions; also, it is possible to have two testing series with respectively three vehicles tires at the same adjustments. Slight deviations in the wear patterns can then be compensated by averaging the results of the respectively two or three simultaneously tested vehicle tires. The six uniformly distributed vehicle wheel receptacles also afford an advantageous distribution of the forces acting on the friction body as well as an especially favorable spatial arrangement.

The permanent friction coating is preferably applied by tamping or casting of the friction material. Preferred friction material is abrasive emery cloth or grindstone material. Grindstone material comprised of a potting resin with broken corundum affords an especially uniform and minimal wear of the friction coating.

Preferably, the friction body is provided with a mantle made of steel which is coated with the friction material.

Friction coatings between 8 mm and 12 mm of thickness allow for a relatively long service life of the friction coating without special constructive problems for ensuring a constant radial pressing force between the vehicle tire and the friction body even for relatively small vehicle tires.

By controlling and adjusting the preset camber angle during the testing period it is possible to simulate certain camber profile patterns. This allows for simulation of the camber angle changes resulting from the driving condition of a vehicle, for example, during load changes or for suspension symmetry changes and their effect on the uniformness of the wear pattern of a vehicle tire. Due to the controllability of the kingpin inclination angle it is possible to simulate tread strip wear occurring at vehicles during operation on a predetermined course with navigation of. This allows for testing the uniformness of the wear behavior for a predetermined course.

By controlling the rotational velocity of the friction body predetermined velocity profiles, which correspond to predetermined velocity changes at the vehicle, can be simulated.

BRIEF DESCRIPTION OF THE DRAWINGS

The object and advantages of the present invention will appear more clearly from the following specification in conjunction with the accompanying drawings, in which.

DESCRIPTION OF PREFERRED EMBODIMENTS

Figure 3:
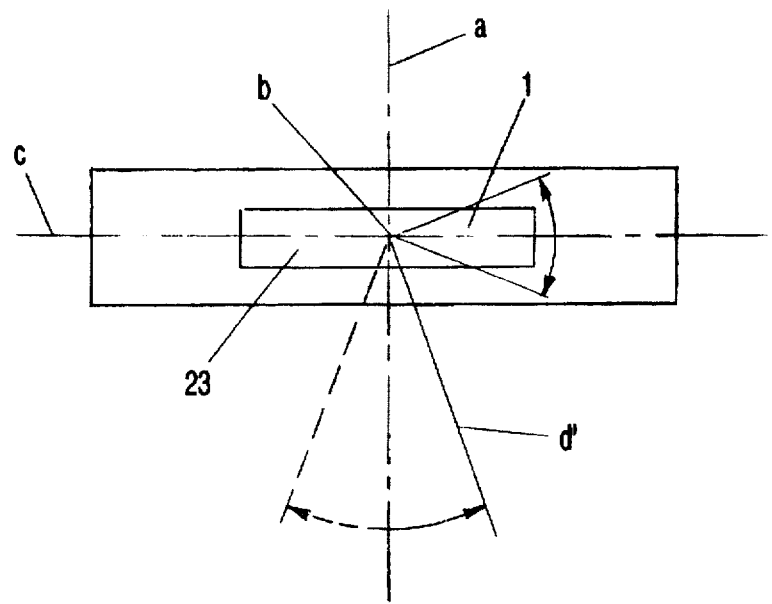
FIG. 3 shows a schematic representation for illustrating the kingpin inclination adjustment.

The present invention will now be described in detail with the aid of several specific embodiments utilizing FIGS. 1 through 3.

Figure 1:
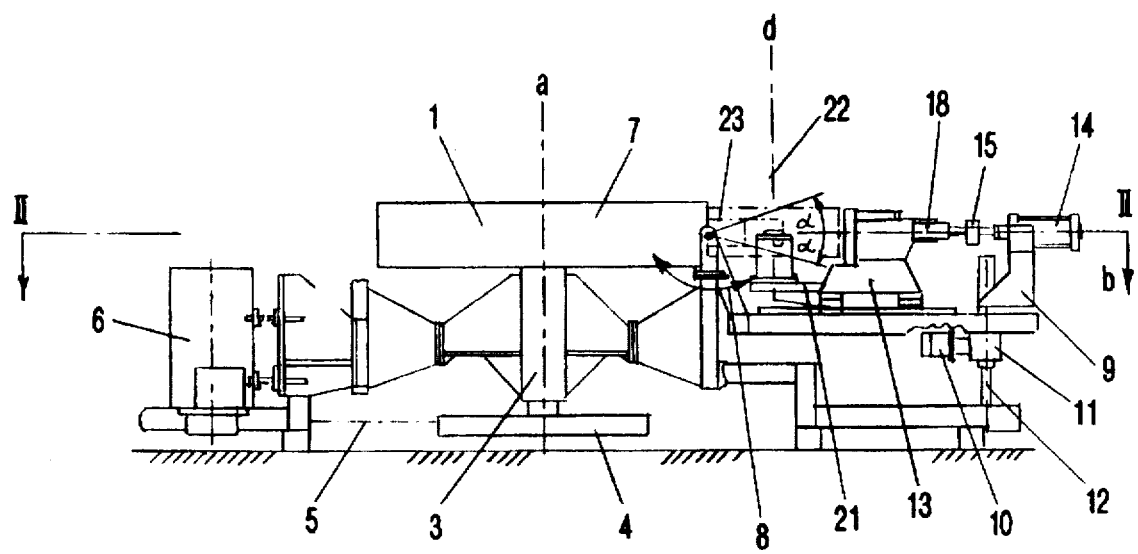
FIG. 1 shows a cross-sectionional representation of the inventive test stand.
Figure 2:
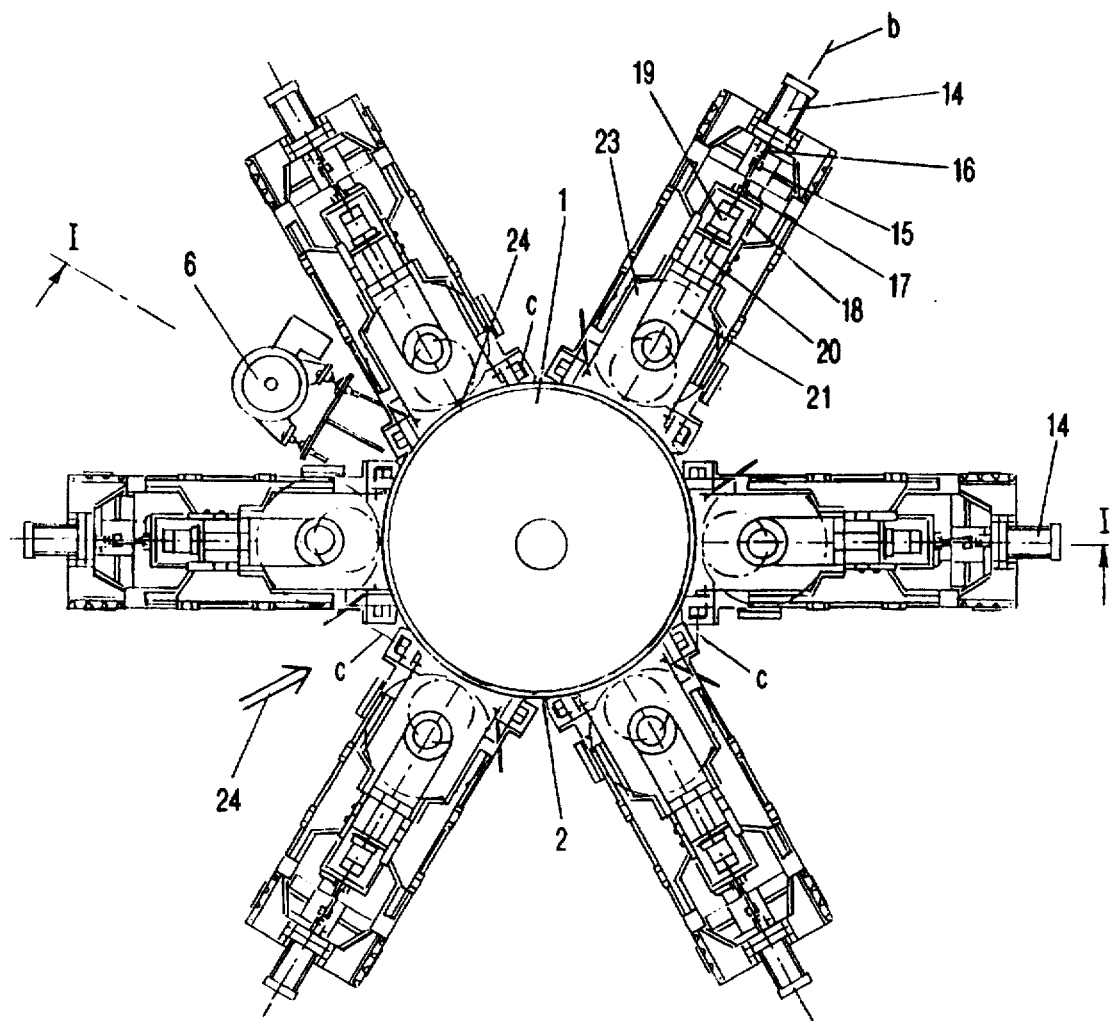
FIG. 2 shows a plan view according to the sectional view II—II of FIG. 1 onto the inventive test stand with six vehicle wheels.

According to the representation in FIGS. 1 and 2, the wear test stand has a central body 7 in which a friction body or drum 1 with its drive shaft 3 is rotatably supported whereby the drive shaft 3, the drive wheel 4, and the drive belt 5 are driven by a motor 6 in a manner known per se. The motor 6 is embodied such that is controllable with respect to its velocity. The friction drum 1 comprises a cylindrical mantle made of steel. This mantle is provided at its circumference in a manner known per se with grindstone material comprised essentially of broken corundum which is embedded in a potting resin and which is uniformly coated by tamping. The friction coating 2 has a uniform thickness of 8 to 12 mm. It is also possible to use any other grindstone material or emery cloth for the friction coating. Also, the friction coating can be produced by casting or by any other method that produces a permanent coating. About the central body 7 six rocker arms 8 with frames 9 connected thereto are uniformly distributed over the circumference of the friction drum so as to be concentric to the axis of rotation A of the friction drum 1. The rocker arms 8 are pivotable tangentially to the friction drum about a pivot axis c. At the end section of each rocker arm 8, radially outwardly relative to the pivot axis c, a control means in the form of a pivot drive including a spindle nut 11 that is rotatably supported and a spindle 12 extending from the bottom to the top through the inner thread of the spindle nut 11 is provided. The spindle, below the spindle nut 11, is supported in an extension of the central body 7 so as to be pivotable about a pivot axis. The control means includes electric motors connected to the respective rocker arms 8 for rotating the spindle nut 11 which is axially fixed about the spindle 12 so that the rocker arm 8 is pivoted about its pivot axis c.

The radially outer end section of each rocker arm 8 is embodied as a frame 9 extending upwardly. Within the frame 9 a pneumatic cylinder 14 is fastened. The piston rod 16 of the pneumatic cylinder 14 extends radially inwardly in the direction toward the axis of rotation a of the friction body 1 and is movable with the aid of the controlled pneumatic cylinder 14. In the extension of the piston axis 14 a load cell 15 and a frame 18 are connected. The frame 18 with its lower portion is fastened to a carriage 13 which is guided radial to the axis a of the friction body 1 toward the rocker arm. By adjusting the pneumatic cylinder 14, the frame 18 can be moved radially inwardly in the direction toward the axis of rotation a or radially outwardly away from it. To the frame 18 a control means in the form of a pivot drive including a three-phase electric motor 19 is fastened which is in driving connection with a shaft 20 of the control means that is concentrically arranged to the axis of the pneumatic cylinder 14 and is rotatably supported within the frame 18. A pivotable bearing plate 21 is fastened to the shaft 20. The pivotable bearing plate 21 comprises at its end facing the friction drum a receptacle 22 for the vehicle wheel 23. The receptacle 22 is rotatably supported on the bearing plate 21. A vehicle wheel 23 is positioned in the receptacle 21 before a wear test and concentrically fastened relative to the axis d. For testing the wear of a vehicle wheel and for simulating wear during driving conditions with a vehicle without camber, respectively, kingpin inclination of the vehicle wheel, i.e., with camber angle, respectively, kingpin inclination angle of 0°, the rocker arm 8 is first pivoted by the spindle 12 about the axis c to such an extent that the axis of the pneumatic cylinder 14 is in a plane perpendicular to the axis of rotation a of the friction drum 1. With the aid of the three-phase electric motor 19 the shaft 20, which in this position is also in a plane parallel to the axis a, and thus also the receptacle 22 are pivoted to such an extent that the axis of rotation d of the vehicle wheel 23 is parallel, and not slanted, relative to the axis of rotation a of the friction drum 1. With the aid of the pneumatic cylinder 14 the vehicle wheel 23 is moved with its tread strip radially onto the friction drum 1 until the tread strip comes into contact with the friction coating 2 at the circumferential surface of the friction drum 1. In a fine adjustment with the load cell 15 the predetermined pressing force between the vehicle wheel 23 and the friction drum 1 is adjusted with the aid of the pneumatic cylinder 14. With the aid of the motor 6 the friction drum 1 with its friction coating 2 is driven for producing the wear test results and the vehicle wheel 23 is frictionally driven about its axis b by the friction drum 1.

After reaching the predetermined simulated mileage, the vehicle wheel 23 is removed in the radially outer direction from the friction coating 2 with the aid of the pneumatic cylinder 14 and is taken out of the receptacle 22 in the upward direction. The wear pattern of the tread strip is then examined.

For measuring the wear of a vehicle tire with predetermined camber adjustment, in a first step, with the aid of the electric motor 10, the spindle nut 11, and the spindle 12, the rocker arm 8 is adjusted to such an extent that the axis b of the pneumatic cylinder 14 has an angle relative to the plane perpendicular to the axis of rotation a of the friction drum 1 which corresponds to the desired camber angle. Subsequently, the vehicle wheel is brought into contact with the friction coating 2 with the aid of the pneumatic cylinder 14 and is loaded with the predetermined pressing force.

For examining the non-uniform wear pattern of a tread strip of a vehicle wheel with predetermined kingpin inclination angle, the shaft 20 is rotated with the aid of the three-phase electric motor 19 such that the pivotable bearing plate 21 with the receptacle 22 is moved out of its initial position, which it assumes during measuring without camber and without inclination angle, about the axis b of the shaft 20. The axis of rotation d of the vehicle wheel is thus moved by an angle β into a position d' that is represented in FIG. 3. The pivoting is carried out until the angle β has the desired, predetermined kingpin inclination angle. Subsequently, the vehicle wheel is moved with the aid of the pneumatic cylinders 14 toward the friction body 1 and, after contacting, is loaded with the desired pressing force.

It is also possible to adjust the camber angle as well as the kingpin inclination angle. For this purpose, the rocker arm 8 is first adjusted with the electric motor 10 until the camber angle α has been reached and subsequently, with the aid of the three-phase electric motor 19, the shaft 20 is rotated until the desired kingpin inclination angle β has been reached.

It is possible to use a controlled motor for driving the spindle and to use a controllable three-phase electric motor 19 for adjusting the shaft 20. With this arrangement, during operation the kingpin inclination angle or the camber angle or both angles can be adjusted. A control allows, for example, the simulation of certain predetermined driving profiles for the kingpin inclination as they, for example, occur during navigation of curves with changing kingpin inclination angle. Also, certain camber angle wear profiles can be simulated as they occur, for example, by changing the suspension symmetry and other load changes with changed camber. With a corresponding design of the drive 6 as a controllable drive it is also possible to simulate velocity control corresponding to a predetermined velocity profile of changing velocities.

The adjustment of the camber angle in the embodiment of FIG. 1 is carried out in a range of +6° to –6°. However, it is also possible to embody the device such that camber angles α can be adjusted over a greater range, for example, between +15° to –15°. The adjustment of the angular range for the kingpin inclination in the embodiment of FIG. 1 is realized for an angular range of +2° to –2°. However, it is also possible to have a kingpin inclination angle range for the angle β that is, for example, between +10° to –10°.

For binding the worn off rubber material it is possible to continuously apply with the aid of the schematically indicated nozzles 24 talc onto the circumferential surface of the friction body 1 so that the worn off material will not collect at the circumferential surface of the friction body and will not impair the friction conditions. It is also possible to remove the worn off material with additional suction devices which are not represented. For a wear test stand with a plurality of vehicle wheels, for example, as indicated in FIGS. 1 and 2, with 6 simultaneously testable vehicle wheels, it is possible to control the parameters for camber angle, kingpin inclination angle, testing period, and radial force for all tires individually, differently, and independent from one another.

It is also possible for the individual testing positions to provide the receptacle 22 with individual additional drives and/or a controlled braking device in order to generate simultaneously differently controlled relative velocities relative to the friction drum 1 even for identical tires.

For controlling the friction coating it is also possible to provide additionally one or more cleaning devices that are distributed uniformly over the circumference of the friction drum. For removing worn-off rubber particles it is, for example, possible to provide fine, soft brushes which are radially applied to the friction drum. These may be rotatably supported brushes.

It is also possible to provide one or more uniformly distributed machining devices (not represented in the drawing) for making more uniform the surface of the friction coating. For example, driven grinding machines with suitable grinding coatings can be advanced to the friction coating, and, if necessary, by driving the friction drum with the aid of the grinding machines during the service life of a friction coating a defined surface roughness can be reproduced uniformly over the circumference of the friction drum.

The present invention is, of course, in no way restricted to the specific disclosure of the specification and drawings, but also encompasses any modifications within the scope of the appended claims.

What we claim is:

1. A device for simulating non-uniform wear on a tread strip of a pneumatic vehicle tire, said device comprising:

a support structure;

a friction body having radial symmetry connected to said support structure so as to be rotatable about a first axis of rotation;

said friction body having a rigid circumferential mantle surface with a circumferentially continuous, permanent friction coating;

a receptacle rotatably connected to said support structure for receiving a vehicle wheel including a pneumatic vehicle tire, wherein the vehicle wheel is rotated about a second axis of rotation with said receptacle;

a load-applying member connected to said receptacle;

said load-applying member extending radially relative to said friction body and acting radially onto said receptacle for pressing the pneumatic vehicle tire of the vehicle wheel onto said friction coating for generating wear at the pneumatic vehicle tire; and a first control means including a motor for pivoting said second axis of rotation of the vehicle wheel about a first pivot axis, extending perpendicular to said first axis of rotation, from a position parallel to said first axis of rotation into a position at an angle to said first axis of rotation for simulating a positioning angle of the vehicle wheel selected from a camber angle and a kingpin inclination angle.

2. A device according to claim 1, further comprising a second control means including a motor for pivoting said second axis of rotation of the vehicle wheel about a second pivot axis, extending perpendicular to said first axis of rotation and in a common plane with said first pivot axis, from a position parallel to said first axis of rotation into a position at an angle to said first axis of rotation, wherein said first and second control means act independently on said receptacle such that pivoting about said first pivot axis simulates the camber angle and pivoting about said second pivot axis simulates the kingpin inclination angle.

3. A device according to claim 2, wherein a plurality of said receptacles with said coordinated load-applying members and said first and second control means are distributed about the circumference of said friction body.

4. A device according to claim 3, wherein six of said receptacles with six of said load-applying members and six of said first and six of said second control means are provided.

5. A device according to claim 1, wherein said friction coating is tamped onto said friction body.

6. A device according to claim 1, wherein said friction coating is cast onto said friction body.

7. A device according to claim 1, wherein said friction coating is comprised of abrasive emery cloth.

8. A device according to claim 1, wherein said friction coating is comprised of grindstone material.

9. A device according to claim 8, wherein said friction coating is comprised of broken corundum embedded in a potting resin.

10. A device according to claim 1, wherein said friction body comprises a steel mantle permanently coated with said friction coating.

11. A device according to claim 1, wherein said friction coating has a radial thickness of 8 mm to 12 mm.

12. A device according to claim 2, wherein said first control means is a controllable pivot drive.

13. A device according to claim 2, wherein said second control means is a controllable pivot drive.

14. A device according to claim 1, wherein said friction body is controllable.

* * * * *